United States Patent [19]

Wehinger et al.

[11] 4,154,839
[45] May 15, 1979

[54] 2,6-DIMETHYL-3-CARBOXYMETHOXY-4-(2-NITROPHENYL)-5-CARBISOBUTOXY-1,4-DIHYDROPYRIDINE

[75] Inventors: Egbert Wehinger, Velbert; Friedrich Bossert, Wuppertal; Arend Heise, Wuppertal; Stanislav Kazda, Wuppertal; Kurt Stoepel, Wuppertal; Wulf Vater, Leverkusen, all of Fed. Rep. of Germany

[73] Assignee: Bayer Aktiengesellschaft, Fed. Rep. of Germany

[21] Appl. No.: 903,573

[22] Filed: May 8, 1978

Related U.S. Application Data

[63] Continuation of Ser. No. 738,383, Nov. 2, 1976, abandoned.

[30] Foreign Application Priority Data

Nov. 5, 1975 [DE] Fed. Rep. of Germany ....... 2549568

[51] Int. Cl.$^2$ .................... C07D 213/55; A61K 31/44
[52] U.S. Cl. ...................................... 424/266; 546/321
[58] Field of Search .................. 260/295.5 R; 424/266

[56] References Cited

U.S. PATENT DOCUMENTS 3,799,934  3/1974  Meyer et al. ................. 260/294.8 G Primary Examiner—Alan L. Rotman
Attorney, Agent, or Firm—Jacobs & Jacobs

[57] ABSTRACT

The isobutyl methyl 1,4-dihydro-2,6-dimethyl-4-(2-nitrophenyl)-3,5-pyridinedicarboxylate demonstrates the unique ability of increasing myocardial perfusion upon oral or intravenous administration. Methods of preparing the compound, its use in coronary conditions and pharmaceutical compositions for effecting that use are disclosed.

5 Claims, No Drawings

2,6-DIMETHYL-3-CARBOXYMETHOXY-4-(2-NITROPHENYL)-5-CARBISOBUTOXY-1,4-DIHYDROPYRIDINE

CROSS-REFERENCE

This is a continuation of Ser. No. 738,383 filed Nov. 2, 1976, now abandoned.

DETAILED DESCRIPTION

The present invention pertains to a new organic compound which demonstrates superior and unexpected properties as a therapeutic agent in coronary conditions.

The preparation of diethyl 1,4-dihydro-2,6-dimethyl-4-phenyl-3,5-pyridinecarboxylate from benzylideneacetoacetic acid ethyl ester and β-aminocrotonic acid ethyl ester (or acetoacetic acid ethyl ester and ammonia) is well known. See e.g., Knoevenagel, Ber. dtsch. chem. Ges. 31, 743 (1898). It is also known that various 1,4-dihydropyridines exhibit coronary vessel dilating properties, as well as hypotensive properties. See e.g., Bossert and Vater, Naturwissenschaften 58, 578 (1971) and German O.S. Nos. 2,117,571 and 2,117,573.

The present invention pertains to isobutyl methyl 1,4-dihydro-2,6-dimethyl-4-(2-nitrophenyl)-3,5-pyridinedicarboxylate which may be graphically depicted by the following formula:

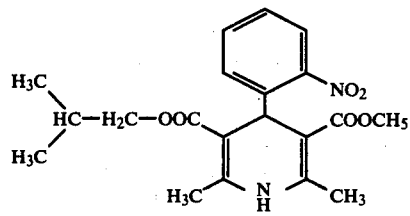

I

As is discussed in greater detail below, this compound exhibits a powerful and long acting effect on coronary perfusion.

The compound may be prepared in a number of different fashions. Isobutyl 2-nitrobenzylideneacetoacetate is allowed to react with methyl β-aminocrotonate, optionally in the presence of water or inert organic solvent, or with the elements of this ester, methyl acetoacetate and ammonia. Alternatively, methyl 2-nitrobenzylideneacetoacetate is allowed to react with isobutyl β-aminocrotonate, again optionally in the presence of water or inert organic solvent, or with the elements of this crotonate, namely isobutyl acetoacetate and ammonia. Isobutyl β-aminocrotonate can also be allowed to react with 2-nitrobenzaldehyde and methyl acetoacetate, again optionally in the presence of water or inert organic solvent, or methyl β-aminocrotonate can be allowed to react with 2-nitrobenzaldehyde and isobutyl acetoacetate, again in water or inert organic solvent.

These reactions may be diagrammatically depicted as follows:

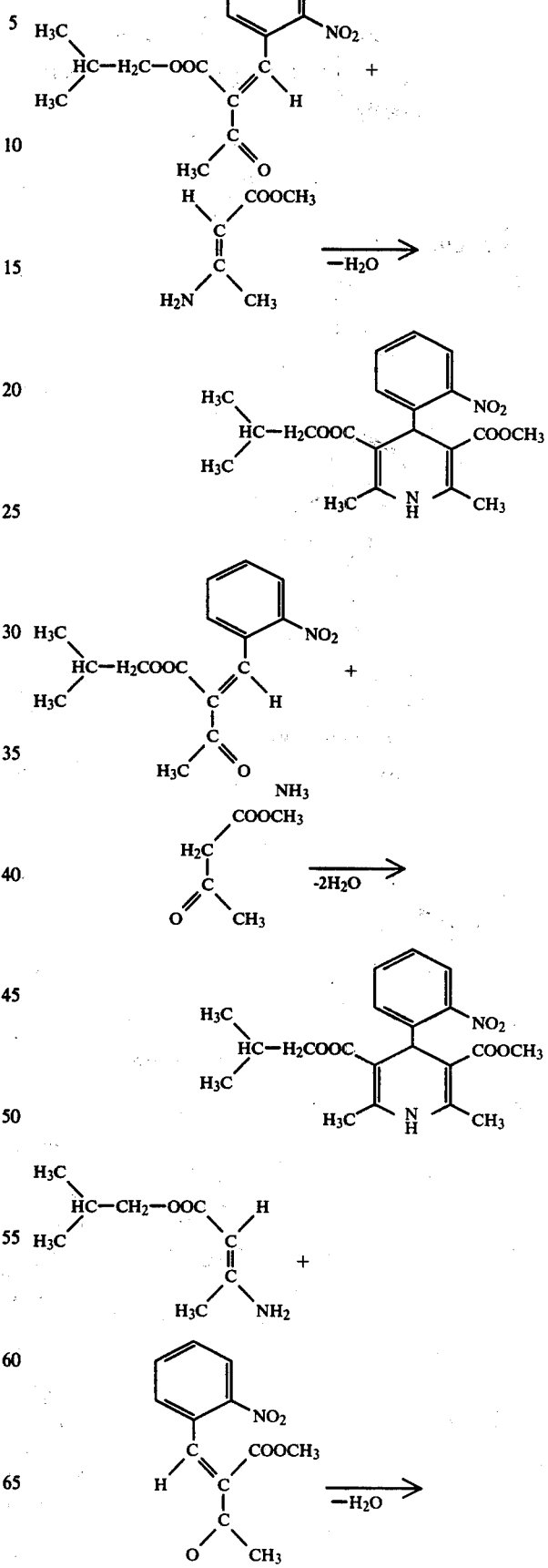

3
-continued

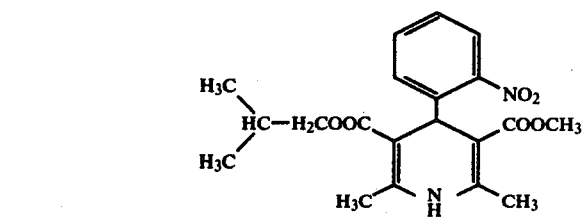

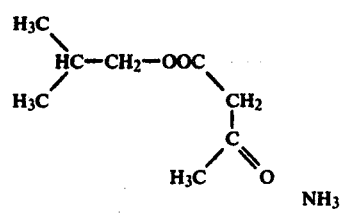 + NH₃

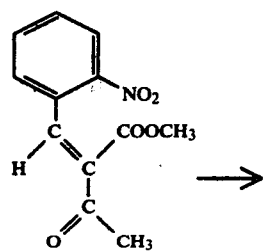 →

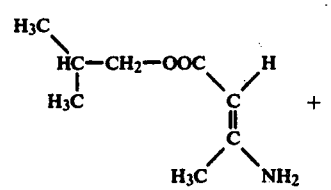 +

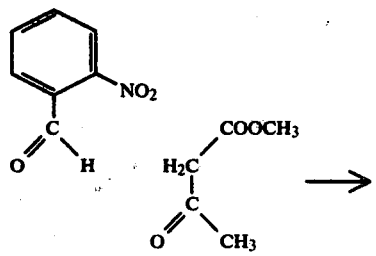 →

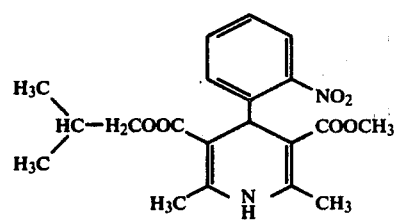

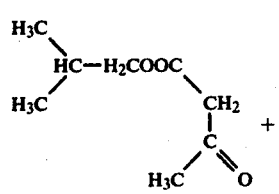 +

4
-continued

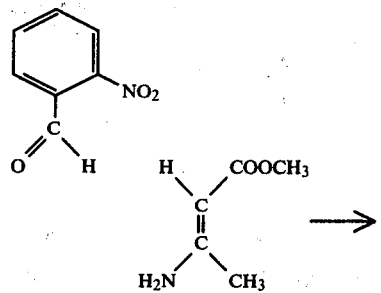 →

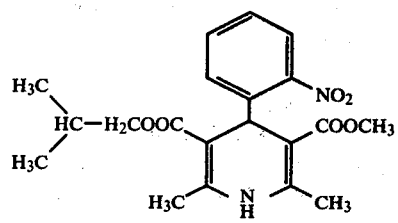

The compound of the present invention has a particularly strong coronary activity which in terms of magnitude and length of action is significantly greater than any 1,4-dihydropyridine presently known. In addition, the compound demonstrates considerably greater stability towards light than previously known 1,4-dihydropyridines, thereby facilitating the formulation of stable pharmaceutical compositions.

It will be appreciated that by reason of the asymmetric pattern of substitution about the 4-carbon atom of the dihydropyridine ring, the compound can exist in enantiomorphic isomers. These can be readily separated, although both isomers appear to possess the disclosed properties, or the racemic mixture of the two can be employed. Both the individual isomers and the racemic mixture are expressly included within the present invention.

The various starting materials are known from the literature and in any event can be prepared in accordance with well known methods; see, e.g. Org. Reactions XV, 204 et seq. (1967); Cope, J. Amer. Chem. Soc. 67, 1017 (1945); and Houben-Weyl, Methods of Organic Chemistry, VII/4, 230 et seq. (1968). Generally the reactants are employed in approximately equal molar amounts, although the ammonia can be advantageously added in excess. The reaction is generally conducted in a diluent such as water or inert organic solvent, as for example, alcohols such as ethanol or methanol, ethers such as dioxane or diethyl ether, glacial acetic acid, pyridine, dimethyl formamide, dimethylsulfoxide or acetonitrile. The reaction temperature can be varied widely and is generally in the range of from about 20° to about 200° C., preferably from about 50° to about 120° C. Most conveniently, the reaction is conducted at the boiling point of the solvent. Although the reaction can be conducted under elevated pressure, in general normal pressures are employed.

The ability of the compound to assist in the perfusion action of the heart muscle can be conveniently observed in recognized pharmacological models. For example, the myocardial perfusion in canines can be observed utilizing an electromagnetic flow meter. Upon sublingual administration to canines, the following pharmacological manifestations are, for example, observed.

| Dose<br>mg/kg<br>sublingual | % Increase in<br>Heart Perfusion | Half-life<br>duration<br>(minutes) | Blood Pressure<br>Decrease (%) |
| --- | --- | --- | --- |
| 0.003 | 23 | 100 | φ |
| 0.01 | 46 | 133 | 5 |
| 0.1 | 142 | 184 | 13 |

It can be seen that the compound increases the perfusion of the heart muscle and that this action is a function of dose. Surprisingly, the effective doses are extremely low. The action commences a few minutes after sublingual administration and, depending upon the dose, lasts for a period of from 2 to 6 hours (the values in the table being half-life rather than total duration). Advantageously, a slight and equally long lasting lowering of blood pressure is also observed.

The compound of the invention is particularly suitable in the prophylaxis and therapy of both acute and chronic ischemic heart disease. It can thus be utilized in the treatment of angina pectoris and conditions following heart infarct. Quite obviously it is particularly suitable in such cases in which elements of hypotension are also present.

The compound can be administered enterally or parenterally. Enterally, the compound is administered via conventional oral techniques, sublingually or rectally. Parenterally, the compound can be given intramuscularly, intraperitoneally or intravenously. Preferably, the compound is given perlingually or intravenously. Generally, a pharmacological response is observed at doses ranging from about 0.0001 to about 1 mg/kg of body weight, preferably about 0.0005 to about 0.01 mg/kg when the route of administration is intravenous. In the case of enteral administration, the dose will be from about 0.0005 to about 10 mg/kg of body weight, preferably from about 0.001 to about 0.1 mg/kg of body weight. These doses are on a daily basis and of course would be suitably subdivided in the case of multiple administration. It will of course at times be necessary to adjust the amount administered and particularly to do so as a function of body weight, route of administration, species, specific condition, response desired and response observed. In some instances, less than the above lower limit may suffice while in others, the upper limit must be exceeded.

The compound of the present invention is administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

The following examples will serve to typify the nature of this invention but should not be construed as a limitation thereof, the invention being defined solely by the appended claims.

EXAMPLE 1

14.6 g (50 mmols) of 2'-nitrobenzylideneacetoacetic acid isobutyl ester together with 5.8 g (50 mmols) of β-aminocrotonic acid methyl ester, in 80 ml of ethanol, were heated for 20 hours under reflux. After the reaction mixture had cooled, the solvent was distilled off in vacuo and the oily residue was mixed with a little ethanol. The product crystallized completely after a short time and was filtered off and recrystallized from ethanol. Melting point: 151°–152° C.—yield: 15.2 g (78%).

EXAMPLE 2

14.6 g (50 mmols) of 2'-nitrobenzylideneacetoacetic acid isobutyl ester together with 5.8 g (50 mmols) of acetoacetic acid methyl ester and 6 ml (88 mmols) of a 25 percent strength aqueous ammonia solution, in 80 ml of methanol, were heated for 24 hours under reflux. The solvent was then distilled off in vacuo and the oily residue was mixed with a little ethanol. The product crystallized completely after a short time and was filtered off and recrystallized from ethanol. Melting point: 150°–152° C.—yield: 11.9 g (61%).

EXAMPLE 3

12.5 g (50 mmols) of 2'-nitrobenzylideneacetoacetic acid methyl ester together with 7.85 g (50 mmols) of β-aminocrotonic acid isobutyl ester in 80 ml of ethanol were heated for 20 hours under reflux. After the reaction mixture had cooled, the solvent was distilled off in vacuo and the solid residue was triturated with ether, filtered off and recrystallized from ethanol. Melting point: 150°–152° C.—yield: 14.5 g (74%).

EXAMPLE 4

12.5 g (50 mmols) of 2'-nitrobenzylideneacetoacetic acid methyl ester together with 7.85 g (50 mmols) of acetoacetic acid isobutyl ester and 6 ml (88 mmols) of a 25 percent strength aqueous ammonia solution, in 80 ml of isobutanol, were heated for 15 hours under reflux. After the reaction mixture had cooled, the solvent was distilled off in vacuo. The oily residue crystallized completely overnight and was triturated with ether, filtered off and recrystallized from ethanol. Melting point: 150°–152° C.—yield: 10.9 g (56%).

EXAMPLE 5

7.85 g (50 mmols) of β-aminocrotonic acid isobutyl ester together with 7.6 g (50 mmols) of 2-nitrobenzaldehyde and 5.8 g (50 mmols) of acetoacetic acid methyl ester in 80 ml of ethanol were heated for 24 hours under reflux. After the reaction mixture had cooled, the solvent was concentrated in vacuo and the solid residue was triturated with ether, filtered off and recrystallized from ethanol. Melting point: 151°–152° C.—yield: 14.5 g (75%).

EXAMPLE 6

5.8 g (50 mmols) of β-aminocrotonic acid methyl ester together with 7,6 g (50 mmols) of 2-nitrobenzaldehyde and 7,85 g (50 mmols) of acetoacetic acid isobutyl ester, in 80 ml of ethanol, were heated to the boil for 24 hours. The solvent was then distilled off in vacuo and the solid residue was recrystallised from ethanol.

Melting point: 151°–152° C.; yield: 13,6 g (70%).

What is claimed is:

1. 2,6-Dimethyl-3-carbomethoxy-4-(2-nitrophenyl)-5-carbisobutoxy-1,4-dihydropyridine.

2. A pharmaceutical composition for increasing coronary perfusion which comprises the compound according to claim 1 in an amount sufficient upon enteral or parenteral administration to a human or other animal to increase coronary perfusion in combination with a pharmaceutical carrier.

3. A composition according to claim 2 wherein the composition is adapted for sublingual administration.

4. A composition according to claim 2 wherein the composition is adapted for intravenous administration.

5. The method of increasing coronary perfusion in humans and other animals which comprises administering to a human or other animal in need of increased coronary perfusion an effective amount of the compound according to claim 1.

* * * * *

UNITED STATES PATENT AND TRADEMARK OFFICE

CERTIFICATE EXTENDING PATENT TERM
UNDER 35 U.S.C. § 156

PATENT NO.      :   4,154,839

ISSUED          :   May 15, 1979

INVENTOR(S)     :   Egbert Wehinger et al.

PATENT OWNER    :   Bayer Aktiengesellschaft

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of Two years from November 2, 1996, the original expiration date of the patent, with all rights pertaining thereto as provided by 35 U.S.C. § 156(b).

I have caused the seal of the Patent and Trademark Office to be affixed this 20th day of November 1997.

Bruce A. Lehman
Assistant Secretary of Commerce and
Commissioner of Patents and Trademarks